United States Patent
Watts et al.

(10) Patent No.: US 6,191,143 B1
(45) Date of Patent: Feb. 20, 2001

(54) TOPICAL ADMINISTRATION OF ANTIMICROBIAL AGENTS FOR THE TREATMENT OF SYSTEMIC BACTERIAL DISEASES

(75) Inventors: Jeffrey L. Watts, Portage; Randall G. Stehle, Kalamazoo, both of MI (US)

(73) Assignee: Pharmacia & Upjohn Company, Kalamazoo, MI (US)

( * ) Notice: Under 35 U.S.C. 154(b), the term of this patent shall be extended for 0 days.

(21) Appl. No.: 09/270,887

(22) Filed: Mar. 17, 1999

Related U.S. Application Data

(62) Division of application No. 08/851,307, filed on Jun. 5, 1997, now Pat. No. 5,929,086.
(60) Provisional application No. 60/041,604, filed on May 10, 1996.

(51) Int. Cl.⁷ .................................................... A61K 31/47
(52) U.S. Cl. ........................................... 514/312; 514/772
(58) Field of Search ...................... 514/312, 772

(56) References Cited

U.S. PATENT DOCUMENTS

| | | |
|---|---|---|
| 3,743,727 | 7/1973 | Herschler . |
| 4,464,367 | 8/1984 | Labeeuw et al. ................... 424/246 |
| 4,486,425 | 12/1984 | Nakao et al. ....................... 424/246 |
| 4,665,079 | 5/1987 | Culbertson et al. ................ 514/312 |
| 4,670,444 | 6/1987 | Grohe et al. ........................ 514/300 |
| 4,754,031 | 6/1988 | Angerbauer et al. ............... 540/225 |

FOREIGN PATENT DOCUMENTS

| | | | |
|---|---|---|---|
| 64740 | 5/1981 | (EP) | ............................. C07D/501/46 |
| 74645 | 3/1983 | (EP) | ............................. C07D/501/46 |
| 0 129 284 | 12/1984 | (EP) | ............................. A61K/47/100 |
| 215650 | 3/1987 | (EP) | ............................. C07D/487/08 |
| 85 00108 | 1/1985 | (WO) | ............................. A61K/31/70 |
| 92 09596 | 6/1992 | (WO) | ............................. C07D/401/04 |

OTHER PUBLICATIONS

Chemical Abstract, vol. 87, No. 6, Aug. 8, 1977, B. Bazhdokov, et al., Dimethyl Sulfoxide As a Carrier of Broad–Spectrum Antibiotics, XP002040745.

Dermatol, Venerol, vol. 16, No. 1, 1977, SOFIA, pp. 33–36.

B. Idson: Percutaneous Absorption Enhancers, Drug & Cosmetic, vol. 137, No. 1, 1985, pp. 30–32, XP002040744.

Chemical Abstract38855, vol. 122, No. 4, Jan. 23, 1995, Abstract CN 1081103A, Jan. 26, 1994 (Faming Zhuanli Shenqing Gongkai Shuomingshu)..

*Primary Examiner*—Rebecca Cook
(74) *Attorney, Agent, or Firm*—Lucy X. Yang; Andrew M. Solomon

(57) ABSTRACT

The present invention provides a method of topically administering antimicrobial agents such as premafloxacin, premafloxacin-like compound, premafloxacin ester, ciprofloxacin, enrofloxacin, cefquinome, cefpodoxime, gentamicin or erythromycin for the treatment of systemic bacterial diseases in mammals.

8 Claims, No Drawings

TOPICAL ADMINISTRATION OF ANTIMICROBIAL AGENTS FOR THE TREATMENT OF SYSTEMIC BACTERIAL DISEASES

CROSS REFERENCE TO RELATED APPLICATIONS

This application is a divisional application of U.S. Ser. No. 08/851,307, filed Jun. 5, 1997 now U.S. Pat. No. 5,929,086; which claims the benefit of U.S. provisional patent application Ser. No. 60/041,604, filed May 10, 1996; which was converted under 37 CFR §1.53 (b)(2) from U.S. patent application Ser. No. 08/644,091, filed on May 10, 1996, now abandoned.

FIELD OF THE INVENTION

The present invention relates to a method of topically administering antimicrobial agents for the treatment of systemic bacterial diseases in mammals.

BACKGROUND OF THE INVENTION

It has been generally accepted that intravenous infusion, intramuscular injection, subcutaneous, buccal, oral, and rectal routes are the methods for administration of a wide variety of antimicrobial agents for the treatment of systemic bacterial diseases. Due to lack of systemic level effects with antimicrobial agents administered topically, the topical administration of antimicrobial agents has been limited to the treatment of localized infections of the skin or eyes.

However, it is known that the aforementioned non-topical methods of administration for the treatment of systemic bacterial diseases have certain disadvantages. For example, buccal and rectal administration often produce discomfort and aggravation to the mammals that are treated. The intravenous, subcutaneous and intramuscular routes are not only painful, but also must be performed by trained individuals. In addition, there is a risk of needle injury, infection, and other trauma including the emotional trauma inevitably associated with injections. Oral administration, although generally acceptable, may have the disadvantages of poor absorption of the therapeutic agent from the gastrointestinal tract and/or degradation which may be caused by the acidic medium of the stomach, or causes digestive disfunction in ruminants. Furthermore, in the case of treating animals, the aforementioned methods of administration are labor and time consuming. Topical administration of antimicrobial agents would circumvent these problems by allowing a more convenient, non-invasive method for the treatment of systemic bacterial diseases.

Thus, it is desirable to have antimicrobial agents that produce systemic effects when they are topically administrated for the treatment of systemic diseases.

It has been unexpectedly discovered, during the investigation of activities of antimicrobial agents by topical administration, that certain antimicrobial quinolones, such as premafloxacin, premafloxacin-like compound, ciprofloxacin, and enrofloxacin, and certain cephalosporin derivatives, such as cefquinome and cefpodoxime, as well as gentamicin and erythromycin, when administrated topically using dimethyl sulfoxide and water as a carrier, are effective for the treatment of systemic bacterial infections. It has also been discovered that premafloxacin, premafloxacin-like compound and its esters, when administrated topically using propylene glycol and oleyl alcohol or propylene glycol and Azone as a carrier, are effective for the treatment of systemic bacterial infections

INFORMATION DISCLOSURE

Premafloxacin, ciprofloxacin, enrofloxacin, danofloxacin, and their quinolone families are series of new and potent antimicrobial agents with a broad spectrum of antimicrobial activity. These quinolone families are active against a variety of human and veterinary pathogens, including both gram-positive and gram-negative bacteria. Premafloxacin and its esters are disclosed in U.S. Pat. Nos. 4,665,079 and 5,563,155, issued May 12, 1987 and Oct. 8, 1996 to Warner-Lambert Company. Ciprofloxacin and enrofloxacin are disclosed in U.S. Pat. No. 4,670,444, issued Jun. 2, 1987 to Bayer Aktiengesellschaft. Danofloxacin is disclosed in European Patent 215650, issued to Pfizer Inc.

Ceftiofur, cefquinome, and cefpodoxime are derivatives of the family of cephalosporins, which have been recognized as highly active antimicrobial agents. Ceftiofur is disclosed in U.S. Pat. No. 4,464,367, issued Aug. 7, 1984 to Sanofi. Cefpodoxime is disclosed in U.S. Pat. No. 4,486,425, issued Dec. 4, 1984 to Sankyo Company Limited. Cefquinome is a known compound which is disclosed in, among the others, U.S. Pat. No. 4,754,031, European Patent 64,740, and European Patent 74,645.

Gentamicin is a known aminoglycoside antibiotic complex derived from *Micromonospora purpurea*, or *M. Echinospora*. Gentamicin is effective against a wide range of aerobic gram-negative bacilli, especially the Enterobacteriaceae and Pseudomonas, and some gram-positive bacteria. Gentamicin is disclosed in, inter alia, U.S. Pat. Nos. 3,091, 572 and 3,136,704.

Erythromycin is an intermediate spectrum macrolide antibiotic, produced by *Streptomyces erythreus*, effective against most gram-positive and certain gram-negetive bacteria. Erythromycin is disclosed in, among the others, U.S. Pat. Nos. 2,653,899 and 2,823,203.

SUMMARY OF THE INVENTION

In one aspect, the present invention provides a method of treating or preventing systemic bacterial diseases in mammals which comprises topically administering to such mammal an effective amount of an antimicrobial agent selected from the group consisting of premafloxacin, premafloxacin-like compound, ciprofloxacin, enrofloxacin, cefquinome, cefpodoxime, gentamicin or erythromycin in a $DMSO/H_2O$ carrier.

In another aspect, the present invention provides a method of treating or preventing systemic bacterial diseases in mammals which comprises topically administering to such mammal an effective amount of premafloxacin, premafloxacin-like compound, or its ester in a PG/OA or a PG/Azone carrier.

DETAILED DESCRIPTION OF THE INVENTION

The present invention resides in the unexpected result that certain antimicrobial quinolones and cephalosporin derivatives as well as gentamicin and erythromycin, when using $DMSO_2O$, as a carrier and when administrated topically, are effective for the treatment of systemic bacterial infections. It is also unexpected that premafloxacin and its esters, when using PG/OA or PG/Azone as a carrier and administrated topically, are effective for the treatment of systemic bacterial infections For the purpose of the present invention, systemic bacterial diseases means systemic bacterial infections caused by a variety of human and veterinary pathogens, including both gram-positive and gram-negative bacteria. Such diseases and conditions are well known and readily diagnosed by physicians and veterinarians of ordinary skill.

The term mammal refers to man and animals of veterinary interest. However, the invention may also be practiced with other vertebrates, and with the lower species comprising the non-vertebrates.

Premafloxacin refers to a compound of formula I or a pharmaceutically acceptable acid addition salt thereof

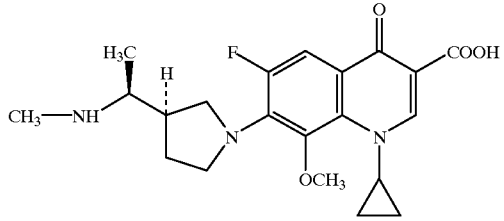

I

Premafloxacin ester refers to a compound of formula II or a pharmaceutically acceptable acid addition salt thereof

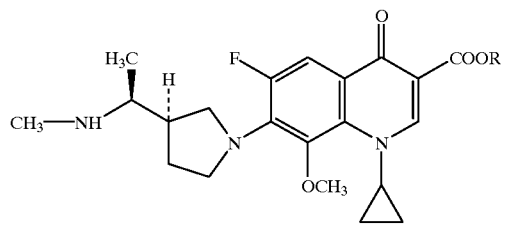

II wherein R is $C_{1-10}$ straight or branched alkyl such as methyl, ethyl, propyl or butyl, $C_{1-10}$ straight or branched alkenyl, $C_{1-6}$ cycloalkyl, phenyl, benzyl, napthyl, or adamantyl.

Premafloxacin-like compound refers to a compound of formula III or a pharmaceutically acceptable acid addition salt thereof

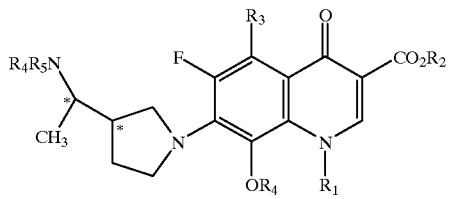

III wherein * denotes an asymmetric carbon atom; $R_1$ is ethyl, cyclopropyl, or 2,4-difluorophenyl; $R_2$ is hydrogen, $C_{1-4}$ alkyl or a cation; $R_3$ is hydrogen, amino, or methyl; $R_4$ and $R_5$ are each independently hydrogen or methyl.

Ciprofloxacin refers to chemical compound of formula IV or a pharmaceutically acceptable acid addition salt thereof

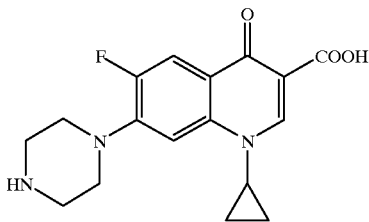

IV

Enrofloxacin refers to chemical compound of formula V or a pharmaceutically acceptable acid addition salt thereof

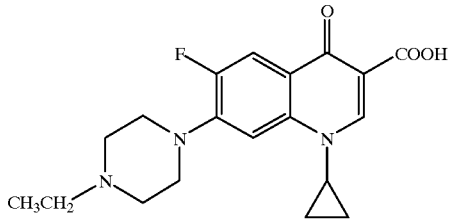

V

Cefpodoxime refers to a compound of formula VI or a pharmaceutically acceptable acid addition salt thereof.

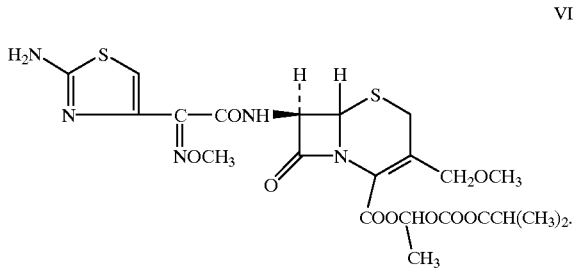

VI

Cefquinome refers to a compound of formula VII or a pharmaceutically acceptable acid addition salt thereof

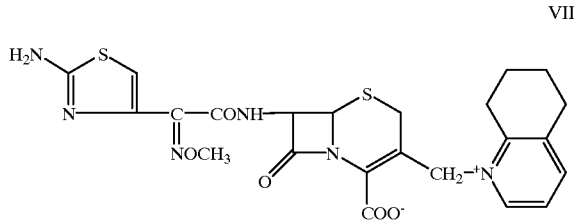

VII

Gentamicin refers to antibiotic complex produced from fermentation of *Micromonospora purpurea* or *M. echinospora* and variants thereof.

Erythromycin refers to antibiotic substance produced by a strain of *Streptomyces erythreus*.

Premafloxacin, ciprofloxacin, enrofloxacin, cefquinome, cefpodoxime, gentamicin and erythromycin are commercially available antibiotic agents. Premafloxacin esters and premafloxacin-like compounds can be prepared according to the procedures described in U.S. Pat. Nos. 4,665,079 and 5,563,155 incorporated herein by reference.

The term DMSO is the abbreviation of dimethyl sulfoxide.

The term PG is the abbreviation of propylene glycol.

The term OA is the abbreviation of oleyl alcohol.

Azone refers to hexahydro-1-dodecyl-2H-azepin-2-one.

The term Ivermectin vehicle refers to the carrier and penetrant used to deliver ivermectin, a commonly used topical antiparasitic agent.

Topical administration or application means the direct contact of an antimicrobial formulation with skin such as, for example, by drops, spray, paint, or pour on. The active antimicrobial formulation of the present invention is administrated 1 to 5 times daily until the bacterial infections is treated.

Topical formulations of this invention may be prepared by employing conventional technique to dissolve an antimicrobial agent described above in DMSO and water, in PG and OA, or in PG and Azone. Optionally, the compositions may contain conventional stabilizers and thickening agents.

For example, an antimicrobial agent is transferred in a DMSO/$H_2O$ carrier, and the mixture is stirred until the solution is clear. When dissolution is complete, the remaining solvents are added to prepare the final concentration of drug and ratio of solvents.

The term DMSO/$H_2O$ carrier refers to the mixture solution of dimethyl sulfoxide and water. MSO and water are in a ratio (DMSO: water) of from 100:0 to about 10:90 by volume to volume (V/V). The use of 100% DMSO by volume achieves the best antimicrobial effect in the present invention, while at least about 10% by volume of DMSO is required in the DMSO and water carrier to have systemic effect.

In another example, about 95% of PG by volume is mixed with about 5% of OA by volume, or about 95% of PG by volume is mixed with about 5% of Azone by volume. An appropriate amount of a premafloxacin ester is weighed out and transferred to the a graduated mixing flask. The desired carrier is then added to the appropriate volume mark. The flask is sealed and the contents is mixed on a rotator until the solution is clear.

The term PG/OA carrier refers to the mixture solution of propylene glycol and oleyl alcohol. Propylene glycol and oleyl alcohol is in a ratio at least about 80% of propylene glycol by volume. The use of 95% propylene glycol and 5% oleyl alcohol achieves the best antimicrobial effect in the present invention.

The term PG/Azone carrier refers to the mixture solution of propylene glycol and Azone. Propylene glycol and Azone is in a ratio at least about 80% of propylene glycol by volume. The use of 95% propylene glycol and 5% Azone achieves the best antimicrobial effect in the present invention.

The amount of an antimicrobial agent in a formulation may be varied or adjusted widely depending upon the solubility of the particular antimicrobial agent, the potency of the particular antimicrobial agent being used, the severity of the bacterial infection, the particular formulation, and the desired concentration. Generally, the amount of an antimicrobial agent is present in the formulation in a range between about 0.5% to about 90% by weight of the formulation, preferably between about 1% to about 25% by weight of the formulation.

In therapeutic use for treating systemic bacterial infections in mammals, an antimicrobial agent is administered topically at a dosage to obtain and maintain a concentration, of which the blood-level of active agent in the mammal being treated is antibacterial effective. Generally, the effective amount of the active agent will be in the range of about 0.1 to about 100 mg/kg, more preferably about 1.0 to about 50 mg/kg of body weight/day. It is understood that the dosages may vary depending upon the requirements of the subject being treated, the severity of the bacterial infection, and the particular antimicrobial agent being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending upon the particular situation.

The present invention achieves the desired results as demonstrated in the mouse systemic protection tests. Mice that had been infected with Pasteurella haemolytica are given doses of a formulation of the present invention. The unexpected result of the present invention is realized by their $ED_{50}$ values. The unexpected results are also demonstrated by the comparison with other routes of administration, with other formulations, and with variety of antimicrobial agents.

In test 1, premafloxacin in an aqueous solution containing 10% DMSO administered topically is compared with premafloxacin administered subcutaneously. Hair is removed from animals in the topically treated group. The $ED_{50}$ for subcutaneous and topical administrations are 0.12 mg/kg of body weight/day and 3.7 mg/kg of body weight/day, respectively.

In test 2, oral administration of premafloxacin is compared with topical administration of premafloxacin. The topical formulation of premafloxacin is prepared using 100% DMSO and is administered to two groups of mice. One group had hair removed while the hair coat is left undisturbed in the second group. The $ED_{50}$s for the three groups were 0.6, 0.87, and 3.4 mg/kg for the oral, topical/hair removed, and topical/no hair removed groups, respectively. It appears that while increasing the DMSO from 10% to 100% increased the penetration of premafloxacin, the hair coat decreased the penetration of the antimicrobial agent.

Test 3 illustrates the antimicrobial effect of various formulations on the activity of topically administered premafloxacin. The data demonstrate that premafloxacin in 100% DMSO formulation achieves the highest antimicrobial activity.

Test 4 lists the antimicrobial effects of several quinolones, cephalosporin derivatives as well as gentamicin and erythromycin in 100% DMSO when administrated topically.

Test 5 illustrates the antimicrobial effect of premafloxacin in a formulation containing PG and OA (95:5 by volume). The result is compared with the antimicrobial effect of premafloxacin in 100% DMSO.

Test 6 lists antimicrobial effects of premafloxacin esters in a formulation containing PG and Azone (95:5 by volume). The antimicrobial effects of premafloxacin esters are compared with the antimicrobial effect of premafloxacin in 100% DMSO and administered orally.

BIOLOGICAL TESTING

1. Bacteria.

The challenge organism, *Pasteurella haemolytica* UC6531, was originally isolated from a case of bovine pneumonia. The organism was kept frozen at −70° C. in trypticase soy broth containing 10% glycerol on 3 mm glass beads. Prior to use, the organism was subcultured onto a trypticase soy agar plate containing 5% sheep blood and incubated for 18–24 hours at 35° C. under aerobic conditions. A single colony was removed from the blood agar plate, inoculated in 6 ml brain-heart infusion broth (BHIB) and incubated for 6 hours at 35° C. in a 5% $CO_2$ atmosphere. The organism was then mixed with an equal volume of BHIB containing 2% brewer's yeast which served as the final inoculum.

2. Mouse Systemic Protection Tests

The *P. haemolytica* mouse systemic protection test was used to evaluate the activity of a new extended spectrum antimicrobial agents by topical administration. For this model, 21–25 day old female CD-1 mice were used. Mice were injected with approximately 100 $LD_{50}$ doses of the challenge organism intraperitoneal. Antimicrobial agents were administered (0.1 ml) either by subcutaneous injection, orally (subcutaneous and oral administration served as positive controls) or by topical administration. For topical administration, the antimicrobial agent was dissolved in the appropriate solution and placed in a 1 $cm^2$ area on the back. All antimicrobial agents were administered within one hour of challenge and at 24 hours intervals for the two following days for a total treatment time of three days. Ten mice were used in each treatment group at each dosage level with five, two-fold serial dilutions of the antimicrobial agent in each determination. The post-challenge effectiveness was calculated based on post-challenge day 6 and was reported as the $ED_{50}$, the amount of antimicrobial agent (mg/kg body weight/day) required to protect 50% of infected mice. Antimicrobial agents with lower $ED_{50}$ values are expected to be more effective. It is generally considered that an agent with a $ED_{50}$ value less than 10 will display efficacious therapeutic effects in treating systemic bacterial diseases in mammals.

TEST 1
Hair is removed from a 1 $cm^2$ area of skin on the front shoulder of mice. Premafloxacin in 10% DMSO is administered topically. The result is compared with a group of mice receiving subcutaneous injection of the same antimicrobial agent.

| Antimicrobial Agent | Administration Route | Formulation | $ED_{50}$ (mg/kg/day) |
|---|---|---|---|
| Premafloxacin | Subcutaneous | Aqueous Solution | 0.12 |
| Premafloxacin | Topical | 10% DMSO | 3.7 |

TEST 2
Topical administration of premafloxacin in 100% DMSO in both denuded and normal mice. The results are compared with oral administration of premafloxacin in aqueous solution.

| Antimicrobial Agent | Administration Route | Formulation | $ED_{50}$ (mg/kg/day) |
|---|---|---|---|
| Premafloxacin | Oral | Aqueous Solution | 0.6 |
| Premafloxacin | Topical (hair removed) | 100% DMSO | 0.87 |
| Premafloxacin | Topical (no hair removed) | 100% DMSO | 3.4 |

TEST 3
Topical administration of the antimicrobial agent in various formulations. Hair was not removed in this test. The results are compared to oral administration of premafloxacin.

| Antimicrobial Agent | Administration Route | Formulation | $ED_{50}$ (mg/kg/day) |
|---|---|---|---|
| Premafloxacin | Oral | Aqueous Solution | 0.6 |
| Premafloxacin | Topical | 100% DMSO | 2.2 |
| Premafloxacin | Topical | Aqueous Solution | >10 |
| Premafloxacin | Topical | Propylene Glycol/ Glycerol Formal (60:40) | >10 |
| Premafloxacin | Topical | PEG 400 | >10 |
| Premafloxacin | Topical | Ivermectin Vehicle | >10 |

TEST 4
Topical administration of various antimicrobial agents in 100% DMSO. Hair was not removed in this test. The results are compared to oral administration of premafloxacin.

| Antimicrobial Agent | Administration Route | Formulation | $ED_{50}$ (mg/kg/day) |
|---|---|---|---|
| Premafloxacin | Oral | Aqueous Solution | 0.9 |
| Premafloxacin | Topical | 100% DMSO | 2.6 |
| Ciprofloxacin | Topical | 100% DMSO | 0.6 |
| Enrofloxacin | Topical | 100% DMSO | 6.7 |
| Danofloxacin | Topical | 100% DMSO | 18.6 |
| Ceftiofur | Topical | 100% DMSO | 15.6 |
| Cefquinome | Topical | 100% DMSO | 3.6 |
| Cefpodoxime | Topical | 100% DMSO | 3.1 |
| Gentamicin | Topical | 100% DMSO | 4.6 |
| Erythromycin | Topical | 100% DMSO | 3.3 |
| Tilmicosin | Topical | 100% DMSO | >50 |

TEST 5
Topical administration of premafloxacin and its esters in formulations containing 95% propylene glycol and 5% oleyl alcohol or 5% Azone. The results are compared with topical administration of premafloxacin in 100% DMSO and oral administration of premafloxacin in aqueous solution.

| Antimicrobial Agent | Administration Route | Formulation | $ED_{50}$ (mg/kg/day) |
|---|---|---|---|
| Premafloxacin | Oral | Aqueous Solution | 1.6 |
| Premafloxacin | Topical | 100% DMSO | 1.7 |
| Premafloxacin | Topical | PG/OA (95:5) | 0.9 |
| Premafloxacin butyl ester | Topical | PG/OA (95:5) | 0.6 |
| Premafloxacin butyl ester | Topical | PG/Azone (95:5) | 0.3 |
| Premafloxacin ethyl ester | Topical | PG/OA (95:5) | 0.7 |
| Premafloxacin ethyl ester | Topical | PG/Azone (95:5) | 0.4 |

We claim:

1. A method of treating a systemic bacterial disease in a mammal in need thereof which comprises topically applying to said mammal an effective amount of an antimicrobial agent in a propylene glycol/hexahydro-1-dodecyl-2H-azepin-2-one (PG/Azone) carrier wherein said antimicrobial agent is selected from the group consisting of premafloxacin or a premafloxacin ester wherein PG and Azone is in a ratio at least about 80% of propylene glycol by volume.

2. A method of treating a systemic bacterial disease in a mammal in need thereof which comprises topically applying to said mammal an effective amount of an antimicrobial agent in a propylene glycol/hexahydro-1-dodecyl-2H-azepin-2-one (PG/Azone) carrier wherein said antimicrobial agent is a compound of formula III or a pharmaceutically acceptable salt thereof

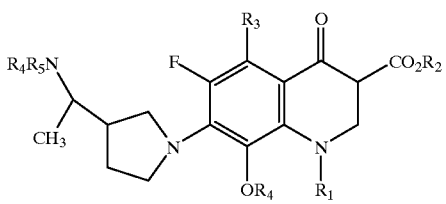
III wherein $R_1$ is ethyl, cyclopropyl, or 2,4-difluorophenyl; $R_2$ is hydrogen or $C_{1-4}$ alkyl $R_3$ is hydrogen, amino, or methyl; $R_4$ and $R_5$ are each independently hydrogen or methyl wherein PG and Azone is in a ratio at least about 80% of propylene glycol by volume.

3. The method of claim 1 or 2 wherein said PG/Azone carrier comprises about 95% of PG and about 5% Azone by volume.

4. The method of claim 1 wherein said premafloxacin ester is a compound of formula II or a pharmaceutically acceptable acid addition salt thereof

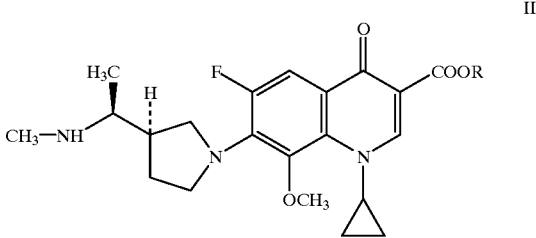
II wherein R is $C_{1-10}$ alkyl, $C_{1-10}$ alkenyl, $C_{1-6}$ cycloalkyl, phenyl, benzyl, or napthyl.

5. The method of claim 4 wherein R is $C_{1-4}$ alkyl.

6. The method of claim 4 wherein R is ethyl or butyl.

7. The method of claim 1 or 2 wherein said antimicrobial agent is topically applied in an amount of from about 0.1 to about 100 mg/kg body weight/per day.

8. The method of claim 1 or 2 wherein said antimicrobial agent is topically applied in an amount of from about 1.0 to about 50 mg/kg body weight/per day.

* * * * *